(12) United States Patent
Archibald et al.

(10) Patent No.: US 8,846,060 B2
(45) Date of Patent: Sep. 30, 2014

(54) SUTURABLE DURAL AND MENINGEAL REPAIR PRODUCT COMPRISING COLLAGEN MATRIX

(75) Inventors: Simon J. Archibald, Pennington, NJ (US); Mark Spilker, Cranbury, NJ (US); Ronald T. Ingram, Encinitas, CA (US); Jeffrey M. Brittan, Encinitas, CA (US)

(73) Assignee: Integra LifeSciences Corporation, Plainsboro, NJ (US)

( * ) Notice: Subject to any disclaimer, the term of this patent is extended or adjusted under 35 U.S.C. 154(b) by 1765 days.

(21) Appl. No.: 11/622,695

(22) Filed: Jan. 12, 2007

(65) Prior Publication Data

US 2007/0161109 A1 Jul. 12, 2007

Related U.S. Application Data

(60) Provisional application No. 60/758,463, filed on Jan. 12, 2006.

(51) Int. Cl.
*A61K 9/00* (2006.01)
*A61F 2/00* (2006.01)
*A61L 27/50* (2006.01)
*A61L 27/24* (2006.01)
*A61B 17/06* (2006.01)

(52) U.S. Cl.
CPC ............. *A61L 27/24* (2013.01); *A61L 2430/32* (2013.01); *A61F 2250/0023* (2013.01); *A61F 2310/00365* (2013.01); *A61F 2/0077* (2013.01); *A61L 27/50* (2013.01); *A61F 2240/001* (2013.01); *A61F 2240/004* (2013.01); *A61F 2310/00982* (2013.01); *A61F 27/56* (2013.01); *A61F 2250/0015* (2013.01); *A61B 17/06166* (2013.01)

USPC .......................... 424/400; 424/422; 424/443

(58) Field of Classification Search
USPC ........................................ 424/400, 422, 443
See application file for complete search history.

(56) References Cited

U.S. PATENT DOCUMENTS

| | | | |
|---|---|---|---|
| 3,157,524 A | 11/1964 | Artandi | |
| 3,520,402 A | 7/1970 | Nichols et al. | |
| 4,963,146 A | 10/1990 | Li | |
| 5,019,087 A | 5/1991 | Nichols | |
| 5,667,839 A | 9/1997 | Berg | |
| 5,997,895 A * | 12/1999 | Narotam et al. | .............. 424/423 |

FOREIGN PATENT DOCUMENTS

| | | |
|---|---|---|
| EP | 1561480 A2 | 8/2005 |
| WO | 93/10731 A1 | 6/1993 |
| WO | 02/09790 A1 | 2/2002 |

OTHER PUBLICATIONS

U.S. Appl. No. 12/501,089.*
International Preliminary Report on Patentability relating to corresponding PCT/US2007/060479.
International Search Report relating to corresponding PCT/US2007/060479.
European Office Action relating to corresponding EP 07717864.8.

* cited by examiner

*Primary Examiner* — Ruth Davis
(74) *Attorney, Agent, or Firm* — Banner & Witcoff, Ltd.

(57) ABSTRACT

A matrix for tissue growth includes: (a) a first layer including a first assembly of collagen fibers; (b) a plurality of projections on a top surface of the first layer; and (c) a second layer bonded to a bottom portion of the first layer and including a second assembly of collagen fibers, wherein the second layer has a lower density than the first layer, and the matrix includes pores effective to support cell growth into the matrix. A method for providing the matrix is also described.

37 Claims, 1 Drawing Sheet

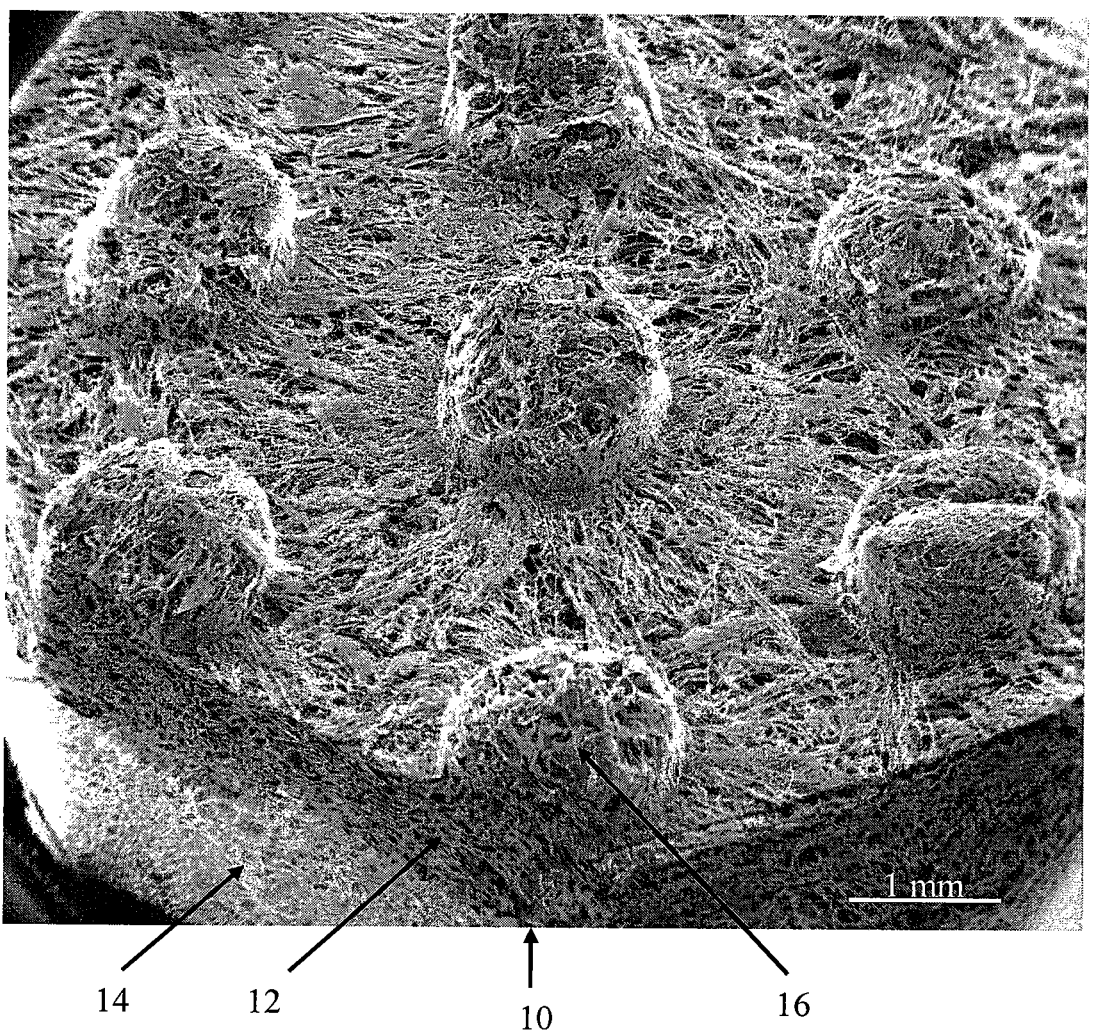

SUTURABLE DURAL AND MENINGEAL REPAIR PRODUCT COMPRISING COLLAGEN MATRIX

BACKGROUND OF THE INVENTION

1. Field of the Invention

This invention relates to the repair of damaged tissue, and more specifically, to the use of noninfectious collagen to heal damaged dural tissue.

2. Description of Related Art

The human brain and spinal cord are covered with meningeal membranes whose integrity is critical to the operation of the central nervous system. When the integrity of a person's meningeal membranes is intentionally or accidentally compromised, serious consequences may ensue, unless the membranes can be repaired.

The meningeal membrane comprises three overlapping layers of tissue, which are in order from outside to inside, the dura mater (or dura), the arachnoid and the pia mater. Repairing damaged meningeal membranes has largely focused on implantable and/or resorbable constructs (known as dural substitutes) which are grafted over the damaged dura mater and are designed to replace and/or regenerate the damaged tissue.

Integra LifeSciences Corp. markets a particularly effective dural substitute under the trademark DURAGEN. The product, which is described in U.S. Pat. No. 5,997,895, comprises a collagen matrix, is fully resorbed following complete tissue closure of the dural defect and easily conforms to complex surfaces. U.S. Pat. No. 5,997,895 discloses that collagen processed using an alkaline/salt treatment in accordance with U.S. Pat. No. 5,019,087 is an extremely effective dural replacement product that will lead to the regeneration of a patient's own functional dura. The preferred alkaline/salt treatment involves sodium hydroxide and sodium sulfate. The methods of U.S. Pat. No. 5,019,087 provide a controlled predictable pore size.

Despite the many benefits of the DURAGEN product, it is desired to provide a further improved dural substitute. In particular, it is desired to provide an improved dural substitute with enhanced suturability. It is further desired that said dural substitute be physiologically compatible (i.e., non-inflammatory, non-adhesion inducing, etc.), sufficiently noninfectious (i.e., decontaminated, etc.) to prevent the transmission of viruses and prions to dural substitute recipients, pliable, available in a variety of sizes, high in tensile strength, inert and optionally capable of forming a water-tight seal.

All references cited herein are incorporated herein by reference in their entireties.

BRIEF SUMMARY OF THE INVENTION

Accordingly, a first aspect of the invention comprises a matrix for tissue growth, said matrix comprising:

a first layer comprising a first assembly of collagen fibers;
a plurality of projections on a top surface of the first layer, wherein the projections have an average diameter of 0.001-0.5 cm and an average height of 0.001-0.2 cm, and wherein at least a part of the top surface of the first layer has at least one projection per square centimeter; and
a second layer bonded to a bottom portion of the first layer and comprising a second assembly of collagen fibers,
wherein the second layer has a lower density than the first layer, and the matrix comprises pores effective to support cell growth into the matrix.

A second aspect of the invention comprises a matrix for tissue growth, said matrix comprising:

a first layer comprising a first assembly of collagen fibers, wherein a top surface of the first layer includes at least one projection and pores having pore sizes ranging from 10 µm to 80 µm, and a bottom portion of the first layer has pores having pore sizes ranging from 80 µm to 250 µm; and
a second layer bonded to the bottom portion of the first layer, and comprising a second assembly of collagen fibers and pores having pore sizes ranging from 10 µm to 500 µm, wherein the second layer has a lower density than the first layer.

A third aspect of the invention comprises a matrix for tissue growth, said matrix comprising:

a first layer comprising a first assembly of collagen fibers, at least one projection on a top surface of the first layer, and first layer pores defined by first layer pore walls; and
a second layer bonded to a bottom portion of the first layer and comprising a second assembly of collagen fibers and second layer pores defined by second layer pore walls,
wherein the first layer has a higher density than the second layer, substantially all of the first layer pores are smaller than substantially all of the second layer pores, and substantially all of the first layer pore walls are thicker than substantially all of the second layer pore walls.

A fourth aspect of the invention comprises a method for providing the matrix of the invention, wherein the method comprises:

providing a first mixture of collagen fibers and a first liquid carrier;
casting the first mixture on a first mold;
draining through the first mold an initial amount of the first liquid carrier to provide a first layer preform;
freezing the first layer preform to provide a frozen first layer preform;
thawing the frozen first layer preform to provide a thawed first layer preform;
compressing the thawed first layer preform against the first mold to drain through the first mold an additional amount of the first liquid carrier to provide the first layer;
providing a second mixture of collagen fibers and a second liquid carrier;
casting the second mixture on the first layer; and
lyophilizing the second mixture on the first layer to provide the second layer on the first layer and thereby provide the matrix.

BRIEF DESCRIPTION OF THE DRAWINGS

The invention will be described in conjunction with FIG. 1, which is a scanning electron micrograph at 35× magnification of an embodiment of a matrix in accordance with the invention.

DETAILED DESCRIPTION OF PREFERRED EMBODIMENTS OF THE INVENTION

The invention provides an improved means for promoting tissue growth. Embodiments of the invention include but are not limited to a matrix and a method for promoting tissue growth, wherein the term "matrix" as used herein refers to an article having pores effective to support cell growth in, around and/or across the article.

Although the matrix and method of the invention are particularly suitable for repairing meningeal tissue (i.e., the dura mater, the arachnoid and/or the pia mater), they are also suitable for promoting tissue growth and/or wound healing in other contexts. For example, the matrix is suitable for use as a bioresorbable pledget to assist in suturing, a suturable hemostatic device, hernia patches, pericardial patches, and the like.

Referring to FIG. 1, matrix 10 preferably comprises at least two layers comprising collagen fibers: (1) a first layer 12 with a relatively high density and relatively small pores; and (2) a second layer 14 with a relatively low density and relatively large pores. The walls of the pores in the first layer are preferably thicker than the walls of the pores in the second layer. The at least two layers are bonded together to form an integral matrix.

The first layer comprises a relatively dense assembly of collagen fibers. A non-woven assembly of fibers is preferred, but other fiber assemblies are within the scope of the invention, including woven fiber assemblies. The matrix can also be provided in the form of a combination of different fiber assemblies. In such an embodiment, all of the fiber assemblies need not be sufficiently porous to promote tissue growth therethrough, as long as at least one sufficiently porous form is accessible to the growing tissue.

The density of the first layer preferably decreases along a gradient from its top surface to its bottom surface (or portion). The first layer has a density of 0.005 mg/mm$^3$ to 0.4 mg/mm$^3$, preferably 0.01 mg/mm$^3$ to 0.1 mg/mm$^3$, more preferably 0.025 mg/mm$^3$ to 0.075 mg/mm$^3$.

The size of the pores of the first layer preferably increases along a gradient from its top surface to its bottom portion. Pores of the top surface of the first layer comprise pore sizes of 10 μm to 250 μm, preferably 30 μm to 150 μm, more preferably 50 μm to 80 μm. Pores of the bottom portion of the first layer comprise pore sizes of 10 μm to 500 μm, preferably 50 μm to 150 μm, more preferably 80 μm to 120 μm.

The relatively high density and relatively low porosity of the first layer provide the matrix with improved strength relative to certain prior art products. The strength of the first layer (and/or the entire matrix) can be quantified by measuring the tear strength using any improvised or standard protocol for measuring tear strength in non-woven materials, such as ISO 9073-4: 1997, ASTM 5733, ASTM 5734 or ASTM 5735. In preferred embodiments, the wet tear strength (i.e., the tear strength of a specimen measured within 5 minutes following a 5-minute immersion in a normal saline solution) is at least 1.5 N, more preferably at least 2.5 N, as measured by an Instron tensile testing machine. The enhanced tear strength renders the matrixes of the invention suitable for suturing to adjacent tissues, although sutures are not required to attach the matrix to such tissues.

The top surface of the first layer preferably includes at least one projection 16, and more preferably includes a plurality of projections. The projections are not particularly limited in size and shape. In preferred embodiments, the quantity, size, shape and placement of the projections are dictated by the first layer preform compression step of the matrix forming method, which is described in greater detail below. In the first layer compression step, fluid is drained from the first layer preform by compressing it against a mold having one or more drainage outlets. Portions of the top surface of the first layer that enter the outlets are molded by compression to form the projections. Thus, the quantity, size, shape and placement of the projections can be adjusted by selecting a mold having the desired number of drainage outlets (i.e., holes), which have the desired dimensions. Table 1 below lists preferred quantity (i.e., density) and size ranges of projections in matrixes according to the invention (wherein the quantity, diameter and height in a given row are independent, and do not necessarily correspond to a single embodiment).

TABLE 1

Preferred Projection Parameter Ranges

| | Quantity (# per cm$^2$) | Average Diameter (cm) | Average Height (cm) |
|---|---|---|---|
| Preferred | 1-500 | 0.001-0.5 | 0.001-0.2 |
| More Preferred | 5-100 | 0.05-0.3 | 0.02-0.2 |
| Most Preferred | 10-20 | 0.1-0.15 | 0.04-0.08 |

In addition to being raised above the top surface of the first layer, the projections are less dense and more porous than the adjacent areas. The outlets in the mold through which the projections are permitted to expand relieve the compressive force experienced by the projections, resulting in projections that are less dense than adjacent areas of the first layer. The projections are therefore more permeable to fluid and tissue infiltration than adjacent portions of the first layer.

In addition to increasing access for fluid and tissue infiltration, the projections aid in reducing graft motion at the tissue interface and increase the surface area for enhanced tissue integration.

The mold can be designed such that the corresponding projections on the matrix collectively convey information, such as the source of the matrix, directions for using the matrix (e.g., the term "UP" to prompt the surgeon to keep that side facing away from the dura), etc.

The second layer is bonded to the bottom portion of the first layer. The term "bonded" as used herein is synonymous with the term "attached". Thus, the nature of the bonding is not particularly limited. In preferred embodiments, the two layers are bonded together by intermingled collagen fibers. The use of adhesives is not required, but is within the scope of the invention.

The second layer preferably comprises a second, preferably non-woven, assembly of collagen fibers, having a second density of 0.001 mg/mm$^3$ to about 0.12 mg/mm$^3$, preferably 0.005 mg/mm$^3$ to 0.1 mg/mm$^3$, more preferably 0.009 mg/mm$^3$ to 0.05 mg/mm$^3$ and a pore size of about 50 μm to about 150 μm. The pore size preferably ranges from about 10 μm to about 500 μm, more preferably from about 50 μm to about 150 μm, with surface pores being smaller than cross-sectional (internal) pores. In particularly preferred embodiments, the pore size of surface pores ranges from about 30 μm to about 150 μm, with about 70 μm being most preferred, and the pore size of cross-sectional pores ranges from about 50 μm to about 300 μm, with about 150 μm being most preferred.

The second layer is intended to be placed in contact with the tissue that is to be grown. The relatively low density and relatively high porosity of the second layer renders it particularly conducive to infiltration by nascent tissue sprouting from adjacent tissue. Preferably, the second layer also permits infiltration by wound fluids and fibrin clots. Fibrin clot formation within the matrix creates a rapid mechanical barrier against CSF leakage.

The matrix can be applied using an onlay or a suturing technique depending on clinical need and surgeon preference. If a surgeon decides to employ sutures, suture bites should preferably taken 2-3 mm from the edge of the graft. Minimum appropriate tension should be applied to the suture when suturing or placing a knot. The use of adhesives, such as fibrin glue, to help bond the matrix to adjacent tissues is optional.

Preferably, the matrix is sufficiently pliable when wet to conform to a surface of an underlying tissue.

Although a two-layered matrix is the preferred embodiment, it is also within the scope of the invention to provide a matrix having three, four, five, or more layers. These additional layers preferably comprise collagen fibers assembled as a non-woven, woven or film. The matrix can be provided in the form of a composite of any two or more of the foregoing forms.

In a preferred embodiment having more than two layers, a third layer is added to the first and second layers described above, wherein the third layer is substantially similar to the first layer and the second layer is sandwiched between the first and third layers. The third layer is preferably a non-woven assembly of collagen fibers bonded to the bottom surface of the second assembly.

The matrix is physiologically compatible and substantially free of viruses and prions.

Preferably, the matrix is a planar object having pores of a sufficient size and quantity to permit growing meningeal tissue to infiltrate said matrix. The length and width of the matrix are dictated by its intended use. Certain embodiments of the matrix are about 1-15 cm in length and width. The thickness of the matrix is related to the number of layers, the height of any projections and the density of each layer. Certain embodiments of the matrix are about 3.0 mm-4.5 mm in thickness.

The matrix can optionally be cross-linked with heat or a suitable chemical cross-linking agent. See, e.g., Chemistry of Protein Conjugation and Crosslinking, (Wong, ed., CRC Press, 1993). For example, by the matrix can be cross-linked by exposure to vapors from an aqueous formaldehyde solution (preferably having a 9.6% formaldehyde concentration) for about ninety minutes at about 25° C., followed by forced air ventilation for about one hour.

The method for producing the matrix of the present invention makes use of steps that are recognized as being effective for inactivating viral and prion contamination. This gives the matrix a very high safety level while eliminating the inflammatory response. That is, the method for producing the matrix of the invention provides a matrix that is substantially free of viruses and prions without being physiologically incompatible. The phrase "substantially free of viruses and prions" means that the matrix does not contain infection-effective amounts of viruses and prions. More specifically, the invention preferably comprises the use of collagen treated by a process sufficient to achieve at least a 4 log clearance of virus, more preferably at least a 6 log clearance of virus, and even more preferably at least an 8 log clearance of virus, as measured with a statistical confidence level of at least 95%. For example, if the concentration of virus before treatment is $10^7$ and after treatment is $10^1$, then there has been a 6 log clearance of virus.

In preparing the matrix of the present invention, a first mixture of collagen fibers and a first liquid carrier is provided. The mixture is preferably a collagen dispersion prepared in a manner well known in the art. One such preparation is taught in U.S. Pat. No. 3,157,524. Another suitable preparation of collagen is taught in U.S. Pat. No. 3,520,402. In certain embodiments, the collagen dispersion is prepared by the following method.

A native source of Type I collagen, such as skin, tendons, ligaments or bone, is first mechanically or hand cleaned of fat, fascia and other extraneous matter and washed. The cleaned and washed collagen containing material is then comminuted, generally by slicing or grinding.

The material is then subjected to an enzyme treatment while under intermittent stirring with a proteolytic enzyme, such as ficin, pepsin, and the like, so as to remove non-collagenous impurities which may cause antigenic activity and to swell the collagen by removing elastin. The amount of enzyme added to the collagen material and the conditions under which enzyme digestion takes place is dependent upon the particular enzyme being used. Generally, when using ficin, which is most commonly used, the pH is adjusted to about 6.0 to 6.3, and the collagen material is digested for about 1 to 2 hours at a temperature of about 36.5° C. to 37.5° C. with one part ficin for every 150 parts of collagen material. After the requisite amount of time, the enzyme is inactivated by appropriate means well known in the art, such as by the addition of a solution of an oxidizing agent, such as sodium chlorite when the enzyme is ficin.

The enzyme treated collagen containing material is then washed to remove excess enzyme and the non-collagenous protein impurities. Preferably, the washing is carried out with ultrafiltered and deionized water and optionally further washed with dilute aqueous hydrogen peroxide.

In a preferred embodiment of the present invention, the enzyme digested collagen containing material is then further subjected to an alkali treatment at a pH of about 13 to 14, at a temperature of about 25° C. to 30° C. for a period of about 35 to 48 hours, preferably about 40 hours. Suitably, the alkali treatment is carried out in an aqueous solution of 5% sodium hydroxide and 20% sodium sulfate. This alkali treatment removes contaminating glycoproteins and lipids. The solution is then neutralized with a suitable acid, such as aqueous sulfuric acid, and thoroughly washed.

The collagen material is then further swollen with a suitable acid solution which acid does not cause any cross-linking of the collagen. Such acids are well known to those skilled in the art and include acetic acid, hydrochloric acid, lactic acid, and the like. Regardless of which acid is used, the pH of the acid collagen dispersion is in the range of about 2 to 3.

The dispersed collagen mixture is then homogenized by any conventional means, such as a blender or homogenizer, so as to further dissociate the fibers and then filtered to remove unswollen, non-collagenous material by means well known in the art, such as by passing the dispersion through a 100 mesh stainless steel screen. The resulting filtered collagen dispersion can then be used to prepare the matrix of the present invention.

Alternatively, physiologically compatible collagen which is substantially free of active viruses and prions can be obtained from transgenic animals bred for the purpose of synthesizing human collagen in a readily harvestible form. See, e.g., U.S. Pat. No. 5,667,839 to Berg. Since transgenic animals can be bred and maintained in controlled environments, which prevent them from carrying infections which must be inactivated, the collagen harvested therefrom is physiologically compatible and substantially free of active viruses and prions without further treatment (although further treatment can be performed for an added measure of safety).

The collagen can be lactic acid derived collagen fibers. Such fibers are produced by a process comprising dispersing a virus and prion free collagen source (e.g., alkali-treated bovine tendon slices) in an aqueous solution of lactic acid (preferably about 85%), homogenizing the dispersion, filtering the homogenized lactic acid dispersion, and precipitating collagen fibers from the homogenized lactic acid dispersion by addition of aqueous ammonium hydroxide (preferably 0.35%) sufficient to adjust the pH to about 4.6-4.9.

Lactic acid derived/ammonium hydroxide precipitated collagen fibers are much longer than fibers produced by mechanical/chemical disruption of raw bovine tendon material. During ammonium hydroxide precipitation, the collagen fibers re-coil and are therefore longer. Longer fibers provide greater strength to the final product. The enhanced strength of products of the invention produced according to this particularly preferred method can be sufficiently strong to be water-tight and suturable without the need for cross-linking, thus allowing the degree of cross-linking to be selected based on the desired rate of bioresorption.

The collagen fibers are dispersed in water to provide the first mixture. In certain embodiments, the first mixture is a dispersion in accordance with the teachings of U.S. Pat. No. 4,963,146. The first mixture is cast on a first mold. The mold is preferably a perforated tray made of a metal, such as aluminum. The mold can comprise a non-stick coating if desired. The quantity and dimensions of perforations through the mold are selected to provide the matrix with desired characteristics, and/or to achieve a desired drainage rate of liquids from the mold.

An initial amount of the liquid carrier in the first mixture on the first mold is then drained by gravity through the perforation(s) to provide a first layer preform on the mold. The first layer preform is preferably frozen and then thawed to release additional moisture. The thawed preform is then compressed against the first mold to drain through the first mold an additional amount of the first liquid carrier, and provide the first layer.

Compression is preferably accomplished by sandwiching the thawed preform between two substantially identical molds. The first and/or second mold is/are pressed against the thawed preform in a direction substantially perpendicular to the planes defined by the surfaces of the molds in contact with the preform. Where the second mold has drainage outlets, the first liquid carrier can drain through both the first and second molds, and the resulting first layer has projections on its top and bottom surfaces. The bottom projections are ultimately obscured by the second layer bonded to the bottom surface of the first layer.

The amount of pressure applied in compression is selected such that the resulting first layer has the desired density and porosity. The collagen matrix is compressed from approximately 10 mm thickness to 1-2 mm and most preferably 1.5 mm. The first layer is preferably provided with the pore size ranges discussed above.

In preferred embodiments, a second mixture of collagen fibers and a second liquid carrier is cast on the first layer in the first mold. The collagen content in the aqueous dispersion is controlled at between 0.5-1.0% w/v with a nominal target of 0.75% w/v. The second mixture can be identical to or different from the first mixture. In certain embodiments, the first and second mixtures are drawn from a common source (e.g., a stock slurry). In certain embodiments, the second mixture is a dispersion in accordance with U.S. Pat. No. 5,997,895.

The second mixture is then lyophilized with the first layer to provide the second layer on the first layer and thereby provide the matrix.

In alternative embodiments, the second layer can be formed as an independent component and then bonded to the first layer using adhesive or other means.

Layers additional to the first and second layers can also be incorporated into the matrix in certain embodiments. Such additional layers can be formed on the underlying layer or formed independently of the matrix and bonded to the underlying layer.

For example, a third layer can be provided on the second layer as follows. First, a third mixture of collagen fibers and a third liquid carrier is provided. The mixture is preferably a dispersion of collagen fibers in water. The third mixture can be identical to or different from the first and/or second mixtures. In certain embodiments, the first, second and/or third mixtures are drawn from a common source.

The third mixture is cast on a second mold. The second mold can be identical to or different from the first mold.

An initial amount of the third liquid carrier is permitted to gravity drain through the second mold to provide a third layer preform. The third layer preform is then frozen and thawed to drain additional liquid therefrom.

The thawed third layer preform is then compressed against the second mold to drain through the second mold an additional amount of the third liquid carrier, and provide the third layer. This step is preferably performed in a manner identical to that used to form the first layer.

The third layer is compressed such that it has a third layer target porosity equivalent to one of the other two layers, of a greater porosity or of a lesser porosity. For example, to provide a three-layered system with the outer two layers comprising a dense tensile matrix, the third layer may contain pores having a pore size within the ranges discussed above with respect to the first and second layers.

The third layer is then placed on the second mixture cast on the first layer prior to lyophilizing the second mixture, to bond the second layer to the first and third layers and thereby provide a three-layered matrix.

In a second example of a three-layered matrix, the dense tensile layer may be contained within two outer layers of low density matrix. In this embodiment, the third layer is cast as a dispersion either independently or directly upon the preceding two layers and is bonded by a lyophilization process to the inner matrix. In this example, the third layer preferably comprises a second non-woven assembly of collagen fibers, having a density of 0.0001 mg/mm$^3$ to about 0.12 mg/mm$^3$ and a pore size of about 50 µm to about 150 µm.

The collagen used in the matrixes of the invention is preferably at least about 80% pure, substantially free of all prion and viral contamination, has less than 0.03 eu/gm endotoxins, has not more than 5% fat content, has at least 10% hydroxyproline content and has not more than 5% ash content. Although it is presently preferred that the product be derived from bovine corium or bovine tendon collagen, the collagen can be obtained from other sources, including other bovine tissues and tissues from other animals, including non-bovine mammals, non-mammalian animals and transgenic animals.

In addition to collagen, certain embodiments of the matrix can include natural and/or synthetic polymers for structural support. The polymers should be biocompatible and/or bioresorbable. Suitable polymers include but are not limited to biocompatible and/or bioresorbable lactides, glycolides, and copolymers thereof, polycaprolactones, polyethylene carbonate, tyrosine polycarbonates, tyrosine polyacids, and polyanhydrides. The molecular weight of the polymer is preferably about 5000 to about 500,000.

Certain embodiments include effective amounts of meningeal tissue growth factors and/or bioactive peptides, such as, e.g., RGD containing peptides, decorin, laminin, merosin, chondroitin sulfate, dermatin sulfate, heparan sulfate, keratin sulfate, basic fibroblast growth factor (bFGF), fibronectin and other integrin ligands, entactin and tenascin. In certain embodiments, an effective amount of such an additive is about 1 µg/mg collagen.

The matrix is preferably nonantigenic in addition to being noninfectious and physiologically compatible.

The matrix is suitable for repairing intentional damage to the meningeal tissues, as in surgery, and consequential damage to the meningeal tissues, as might occur as a result of accidental head trauma.

After brain surgery, the matrix of the present invention is inserted to occupy space left by the removal resultant on surgery. As to meningeal repair following a craniotomy or a laminectomy, particularly with the incision through the dura, the matrix of the present invention can simply be implanted in contact with the cranial or spinal dura defect created by the surgery. In addition to simply contacting the damaged meningeal tissue and adjacent undamaged tissue with the matrix (particularly when the matrix is being used as a cranial dura substitute), the matrix can also be mechanically bonded (e.g., sutured) and/or chemically bonded to the damaged tissue and adjacent undamaged tissue (e.g., fibrin glue) repair, especially if used in skull base procedures or intradural spinal surgery.

The matrix preferably connects undamaged portions of meningeal tissue adjacent to the damaged meningeal tissue by overlapping these undamaged tissues. The damaged tissue can be, e.g., torn, cut, excised or lacerated, and can be located in, e.g., the human spinal dura or the human cerebral dura. Regenerated meningeal tissue grows within the matrix, while the matrix remains implanted within a patient. That is, the matrix acts as a scaffold for tissue growth, such as for reparative tissue growth.

Preferably, the matrix is substantially resorbed within about three months after implantation. It is also preferred that the matrix be resorbed at substantially the same rate as new tissue forms.

The invention will be illustrated in more detail with reference to the following Examples, but it should be understood that the present invention is not deemed to be limited thereto.

EXAMPLES

Example 1

Pig Duraplasty Study

The following procedure was conducted on each of five pigs. A bilateral durectomy was performed on the frontal sinus. Substantially identical left and right wounds of about 1×2 cm each were created in the dura.

One of the dural wounds was repaired with a matrix in accordance with the present invention. The matrix of the present invention comprised a stiff white planar sheet having two distinct surface textures, one surface being smooth and the opposite surface being covered with a multitude of circular projections of approximately 1.25 mm in diameter and 0.4-0.8 mm in height. On hydration in normal saline the inventive matrix becomes pliant and conforms easily to the convexity of the exposed brain tissues and dura. The inventive matrix was applied as an overlay and sutured to adjacent dura with 4-0 Nuralon.

The other dural wound (the right side in three of the five pigs) was repaired with a prior art matrix (DURAGEN PLUS, supplied by Integra LifeSciences Corp., Plainsboro, N.J.), which was applied as an overlay without suturing.

The frontal sinus region was reconstructed following implantation of the matrixes. The pigs were sacrificed 90 days after surgery. Healing of the wounds was compared by visual inspection of the dura prior to removing the brain from the skull. In addition, the brain and dura in the region of the wounds were sectioned, stained and mounted for microscopic analysis.

Dural administration of the inventive matrix material, sutured or onlayed, for approximately 90 days in a porcine model resulted in the formation of a neo-dura, similar to that of DURAGEN PLUS. At 90 days following application, the regenerated neo-dural thickness following repair of the dural defect with the inventive device was approximately two-thirds the thickness of adjacent native dura. No significant adverse reactions associated with the test material in either the adjacent meningeal or neural tissues. The onlay and sutured administration of the inventive matrix devices were equivalent to DURAGEN PLUS in their ability to regenerate neo-dura spanning the duraplasty site.

While the invention has been described in detail and with reference to specific examples thereof, it will be apparent to one skilled in the art that various changes and modifications can be made therein without departing from the spirit and scope thereof.

What is claimed is:

1. A matrix for tissue growth, said matrix comprising:
   a first layer comprising a first assembly of collagen fibers;
   a plurality of molded projections extending from a planar top surface of the first layer, wherein the projections have an average diameter of 0.001-0.5 cm and an average height of 0.001-0.2 cm, and wherein at least a part of the top surface of the first layer has at least one projection per square centimeter and wherein the plurality of projections are less dense and more porous than adjacent areas on the top surface; and
   a second layer bonded to a bottom portion of the first layer and comprising a second assembly of collagen fibers, wherein the second layer has a lower density than the first layer, and the matrix comprises pores effective to support cell growth into the matrix.

2. The matrix of claim 1, wherein the projections have an average diameter of 0.05-0.3 cm and an average height of 0.02-0.2 cm.

3. The matrix of claim 1, wherein the first and second assemblies are non-woven.

4. The matrix of claim 3, wherein at least a part of the top surface of the first layer has at least five projections per square centimeter.

5. The matrix of claim 3, wherein the projections collectively convey information.

6. The matrix of claim 3, wherein the matrix is sufficiently pliable when wet to conform to a surface of an underlying tissue.

7. The matrix of claim 3, wherein the matrix is adapted to adhere to the underlying tissue without any added adhesive.

8. The matrix of claim 3, wherein the first layer has a wet tear strength of at least 1.5 N.

9. The matrix of claim 3, wherein the matrix is physiologically compatible and substantially free of viruses and prions.

10. The matrix of claim 3, wherein the matrix is substantially free of adhesives.

11. The matrix of claim 3, wherein the pores adjacent to the top surface of the first layer comprise pore sizes ranging from 10 μm to 80 μm, the pores of the bottom portion of the first layer comprise pore sizes ranging from 80 μm to 250 μm, and the pores of the second layer comprise pore sizes ranging from 10 μm to 500 μm.

12. The matrix of claim 11, wherein second layer pores proximate to a bottom surface of the second layer are outermost pores ranging in size from about 30 μm to about 150 μm and a balance of the second layer pores are innermost pores ranging in size from about 50 μm an to about 300 μm.

13. The matrix of claim 12, wherein the outermost pores are about 70 μm in size and the innermost pores are about 150 μm in size.

14. The matrix of claim 3, wherein the pores adjacent to the top surface of the first layer comprise pore sizes ranging from 50 μm to 80 μm, the pores of the bottom portion of the first layer comprise pore sizes ranging from 80 μm to 120 μm, and the pores of the second layer comprise pore sizes ranging from 50 μm to 150 μm.

15. The matrix of claim 3, wherein the pores adjacent to the top surface of the first layer comprise pore sizes ranging from 10 µm to 250 µm, the pores of the bottom portion of the first layer comprise pore sizes ranging from 10 µm to 500 µm, and the pores of the second layer comprise pore sizes ranging from 10 µm to 500 µm.

16. The matrix of claim 3, wherein the matrix is cross-linked.

17. The matrix of claim 3, wherein the collagen fibers are derived from a bovine source.

18. The matrix of claim 3, wherein the collagen fibers are obtained by a process comprising alkalinizing a collagen containing material to a pH of about 13 to about 14 to substantially remove contaminating glycoproteins and lipids.

19. The matrix of claim 3, further comprising a third layer comprising a third non-woven assembly of collagen fibers bonded to a bottom surface of the second assembly.

20. The matrix of claim 19, wherein the first layer and the third layer are substantially identical.

21. The matrix of claim 3, wherein the pores are of a sufficient size and quantity to permit infiltration by wound fluids and fibrin clots.

22. The matrix of claim 1 wherein the plurality of molded projections have a preselected quantity, size, shape and placement.

23. A matrix for tissue growth, said matrix comprising:
   a first layer comprising a first assembly of collagen fibers, wherein a planar top surface of the first layer includes at least one molded projection extending from the planar top surface and pores having pore sizes ranging from 10 µm to 80 µm, and a bottom portion of the first layer has pores having pore sizes ranging from 80 µm to 250 µm; and
   a second layer bonded to the bottom portion of the first layer, and comprising a second assembly of collagen fibers and pores having pore sizes ranging from 10 µm to 500 µm, wherein the second layer has a lower density than the first layer.

24. The matrix of claim 23, wherein the pores of the second layer have pore sizes ranging from 50 µm to 150 µm.

25. The matrix of claim 23, wherein at least a part of the top surface of the first layer has at least one projection per square centimeter.

26. The matrix of claim 23, wherein at least a part of the top surface of the first layer has at least five projections per square centimeter.

27. A matrix for tissue growth, said matrix comprising:
   a first layer comprising a first assembly of collagen fibers, at least one molded projection extending from a planar top surface of the first layer, and first layer pores defined by first layer pore walls; and
   a second layer bonded to a bottom portion of the first layer and comprising a second assembly of collagen fibers and second layer pores defined by second layer pore walls, wherein the first layer has a higher density than the second layer, substantially all of the first layer pores are smaller than substantially all of the second layer pores, and substantially all of the first layer pore walls are thicker than substantially all of the second layer pore walls.

28. The matrix of claim 27, wherein at least a part of the top surface of the first layer has at least one projection per square centimeter.

29. The matrix of claim 27, wherein at least a part of the top surface of the first layer has at least five projections per square centimeter.

30. The matrix of claim 27, wherein the pores adjacent to the top surface of the first layer comprise pore sizes ranging from 10 µm to 250 µm, the pores of the bottom portion of the first layer comprise pore sizes ranging from 10 µm to 500 µm, and the pores of the second layer comprise pore sizes ranging from 10 µm to 500 µm.

31. The matrix of claim 27, wherein the pores adjacent to the top surface of the first layer comprise pore sizes ranging from 50 µm to 80 µm, the pores of the bottom portion of the first layer comprise pore sizes ranging from 80 µm to 120 µm, and the pores of the second layer comprise pore sizes ranging from 50 µm to 150 µm.

32. A method for providing the matrix of claim 1, comprising providing a first mixture of collagen fibers and a first liquid carrier;
   casting the first mixture on a first mold;
   draining through the first mold an initial amount of the first liquid carrier to provide a first layer preform;
   freezing the first layer preform to provide a frozen first layer preform;
   thawing the frozen first layer preform to provide a thawed first layer preform;
   compressing the thawed first layer preform against the first mold to drain through the first mold an additional amount of the first liquid carrier to provide the first layer;
   providing a second mixture of collagen fibers and a second liquid carrier;
   casting the second mixture on the first layer; and
   lyophilizing the second mixture on the first layer to provide the second layer on the first layer and thereby provide the matrix.

33. The method of claim 32, wherein the first and second liquid carriers are water and the first and second mixtures are dispersions.

34. The method of claim 32, wherein the collagen fibers are derived from a bovine source.

35. The method of claim 32, wherein the collagen fibers are obtained by alkalinizing a collagen containing material to a pH of about 13 to about 14 to substantially remove contaminating glycoproteins and lipids.

36. The method of claim 32, wherein said matrix is a planar object, the pores adjacent to the top surface of the first layer comprise pore sizes ranging from 10 µm to 80 µm, the pores of the bottom portion of the first layer comprise pore sizes ranging from 80 µm to 250 µm, and the pores of the second layer comprise pore sizes ranging from 50 µm to 150 µm.

37. The method of claim 32, further comprising:
   providing a third mixture of collagen fibers and a third liquid carrier;
   casting the third mixture on a second mold;
   draining through the second mold an initial amount of the third liquid carrier to provide a third layer preform;
   freezing the third layer preform to provide a frozen third layer preform;
   thawing the frozen third layer preform to provide a thawed third layer preform;
   compressing the third layer preform against the second mold to drain through the second mold an additional amount of the third liquid carrier to provide the third layer;
   placing the third layer on the second mixture cast on the first layer prior to the lyophilizing second mixture, to bond the second layer to the first layer and the third layer and thereby provide a three-layered matrix.

* * * * *